United States Patent
De Clerck

(10) Patent No.: US 11,376,025 B2
(45) Date of Patent: Jul. 5, 2022

(54) BONE ANCHOR WITH A DRILLING TEMPLATE CONNECTING TO THIS BONE ANCHOR AND METHOD FOR MANUFACTURING THE BONE ANCHOR AND THE DRILLING TEMPLATE

(71) Applicant: TITA-LINK B.V.B.A., Tervuren (BE)

(72) Inventor: Hugo De Clerck, Tervuren (BE)

(73) Assignee: TITA-LINK B.V.B.A., Tervuren (BE)

( * ) Notice: Subject to any disclaimer, the term of this patent is extended or adjusted under 35 U.S.C. 154(b) by 98 days.

(21) Appl. No.: 15/571,883

(22) PCT Filed: May 9, 2016

(86) PCT No.: PCT/IB2016/052637
§ 371 (c)(1),
(2) Date: Nov. 6, 2017

(87) PCT Pub. No.: WO2016/181286
PCT Pub. Date: Nov. 17, 2016

(65) Prior Publication Data
US 2018/0132870 A1    May 17, 2018

(30) Foreign Application Priority Data

May 8, 2015    (BE) .............................. BE 2015/0136

(51) Int. Cl.
*A61B 17/17*    (2006.01)
*A61C 8/00*    (2006.01)
(Continued)

(52) U.S. Cl.
CPC .......... *A61B 17/1728* (2013.01); *A61B 6/032* (2013.01); *A61B 6/14* (2013.01);
(Continued)

(58) Field of Classification Search
CPC ..... A61C 8/0031; A61C 7/02; A61B 17/1728; A61B 17/1673; A61B 17/17;
(Continued)

(56) References Cited

U.S. PATENT DOCUMENTS

| | | | | |
|---|---|---|---|---|
| 5,439,381 A | * | 8/1995 | Cohen ................... | A61C 8/0033 433/177 |
| 2002/0031747 A1 | * | 3/2002 | Laster .................. | A61C 8/0009 433/201.1 |

(Continued)

FOREIGN PATENT DOCUMENTS

| WO | 02091941 A1 | 11/2002 |
|---|---|---|
| WO | 2015017677 A1 | 2/2015 |

OTHER PUBLICATIONS

Janghyun Paek et al., "Virtually fabricated guide for placement of the C-tube miniplate", American Journal of Orthodontics and Dentofacial Orthopedics, pp. 694-702, vo. 145, No. 5 (May 2014).

(Continued)

*Primary Examiner* — Yogesh P Patel
(74) *Attorney, Agent, or Firm* — Browdy and Neimark, PLLC

(57) ABSTRACT

The invention relates to a method for manufacturing at least one bone anchor and a corresponding drilling template, wherein the bone anchor has an anchor plate which is to be fixed to the surface of a bone by means of one or several screws having a screw head. The anchor plate thus has a bone side which is to connect to the surface of the bone and a free side which is opposite to said bone side. Further, the invention concerns a method for manufacturing a drilling template making it possible to make bore holes in the bone at predetermined positions and to screw the bone anchor to said bone according to predetermined orientations.

9 Claims, 3 Drawing Sheets

(51) Int. Cl.

| | |
|---|---|
| *A61C 1/08* | (2006.01) |
| *A61C 13/00* | (2006.01) |
| *A61B 34/10* | (2016.01) |
| *A61B 6/03* | (2006.01) |
| *A61B 6/14* | (2006.01) |
| *A61B 6/00* | (2006.01) |
| *A61B 17/16* | (2006.01) |
| *A61C 7/02* | (2006.01) |
| *A61B 17/00* | (2006.01) |

(52) U.S. Cl.
CPC ........ *A61B 6/4085* (2013.01); *A61B 17/1673* (2013.01); *A61B 17/176* (2013.01); *A61B 34/10* (2016.02); *A61C 1/084* (2013.01); *A61C 7/02* (2013.01); *A61C 8/0019* (2013.01); *A61C 8/0031* (2013.01); *A61C 8/0075* (2013.01); *A61C 8/0089* (2013.01); *A61C 8/0096* (2013.01); *A61C 13/0003* (2013.01); *A61B 2017/00526* (2013.01); *A61B 2034/105* (2016.02); *A61B 2034/108* (2016.02)

(58) Field of Classification Search
CPC ....... A61B 17/176; A61B 34/10; A61B 6/032; A61B 6/14; A61B 6/4085; A61B 1/084; A61B 2017/00526
See application file for complete search history.

(56) References Cited

U.S. PATENT DOCUMENTS

| | | | |
|---|---|---|---|
| 2005/0033430 | A1 | 2/2005 | Powers et al. |
| 2013/0071811 | A1* | 3/2013 | Groscurth .............. A61C 1/084 433/75 |
| 2021/0205119 | A1* | 7/2021 | De Clerck .............. A61F 5/566 |
| 2021/0378787 | A1* | 12/2021 | De Clerck ......... A61C 13/0004 |
| 2021/0386513 | A1* | 12/2021 | Kofron ................ A61C 8/0089 |

OTHER PUBLICATIONS

Jan Hourfar et al., "Fully customized placement of orthodontic miniplates: a novel clinical technique", Head & Face Medicine, p. 14, vol. 10, No. 1 (May 2014).

* cited by examiner

BONE ANCHOR WITH A DRILLING TEMPLATE CONNECTING TO THIS BONE ANCHOR AND METHOD FOR MANUFACTURING THE BONE ANCHOR AND THE DRILLING TEMPLATE

The invention relates to a method for manufacturing at least one bone anchor and a corresponding drilling template, wherein the bone anchor has an anchor plate which is to be fixed to the surface of a bone by means of one or several screws having a screw head. The anchor plate thus has a bone side which is to connect to the surface of the bone and a free side which is opposite to said bone side.

Further, the invention concerns a method for manufacturing a drilling template making it possible to make bore holes in the bone at predetermined positions and to screw the bone anchor to said bone according to predetermined orientations.

According to the present state of the art, bone anchors or other implants are already fastened to bones by means of screws. To this end, a drilling template is manufactured having drill guides for making bore holes for screws in the bone according to predetermined orientations and positions.

After these bore holes have been made by means of the drilling template, said template is removed and the implant to be provided is positioned opposite the bone and then fixed by fastening it with screws in the previously made bore holes.

Such a method is time-consuming, however, since the drilling template must be first positioned against the bone and, after the necessary bore holes have been made, the drilling template must be removed again. Next, the implant is placed against the bone and the screws must be tightened in the bore holes. The latter is sometimes quite difficult since the bore holes are situated behind the implant and the positioning of the implant is often not exactly in line with the position of the bore holes.

The invention aims to remedy these disadvantages by suggesting an implant, or a bone anchor, and a corresponding drilling template which make it possible to position the implant exactly opposite the bore holes which have been provided to fix the implant. When using the bone anchor and the drilling template according to the invention, it is moreover no longer necessary to position the implant again once the drilling template has been removed.

Further, a major application of the bone anchor is the treatment of patients having a malocclusion whereby the lower jaw exhibits a protrusion or a retracted position in relation to the upper jaw. When treating patients with a protrusion of the lower jaw, a first bone anchor is fixed infra-orbitally to the maxilla on either side of the dental arch. The fixing element which extends in the oral cavity is hereby elastically connected to a second bone anchor, also called counter anchor, which is fixed to the lower jaw in the vicinity of the corresponding canine. Thanks to this elastic connection, there is always some tensile stress between both bone anchors. In this manner, the bone of the upper jaw where the first bone anchor has been fixed is gradually moved forward in relation to the lower jaw. Such a treatment is particularly interesting for patients having what is called a class III malocclusion. This treatment also makes it possible to bring certain bone parts such as for example the zygoma more forward in patients with a rather flat face structure, so that for example a face with more pronounced cheek bones is obtained. In certain cases it is even possible to increase the vertical length of the face to some extent.

This treatment gives particularly good results in young patients where the sutures between the various pieces of bone of the skull have not yet fully grown together and still show a certain degree of elasticity. Thus, it is important to start the treatment at the earliest possible age.

At present, however, the age at which one can start with such a treatment with bone anchors is set at 11 years. Indeed, it appears that in young children, the upper jaw, in particular the infrazygomatic arch of the maxilla, is not sufficiently developed yet for fixing a bone anchor to it.

This problem also arises with patients suffering from clefts, whereby in many cases the infrazygomatic arch of the maxillar bone is of insufficient quality or strength to fix a bone anchor to.

Moreover, in young children, the bone of the lower jaw is often insufficiently developed to fix a bone anchor to in a reliable and sufficiently solid manner. Additionally, there is also the danger for the roots of the teeth, or tooth germs, to be damaged when fixing a bone anchor to the lower jaw. This applies for example in particular with respect to the lower jaw, to the roots of the canines or the tooth germs for the canines.

In general, the existing bone anchors, as described for example in WO 02/091941, are disadvantageous in that they cannot be used in persons having an insufficiently or poorly developed bone in the under or upper jaw or having bones with a weak structure. This is for example the case in young children or cleft patients.

When at a later age, a protrusion or retracted position of the lower jaw must be remedied, however, it is usually necessary to achieve this by surgery. In case of a protrusion of the lower jaw, for example, it will be shortened by means of surgery. In the case of a retracted position of the lower jaw in relation to the upper jaw, the upper jaw can be surgically moved somewhat forward. It is clear that these methods entail a relatively time-consuming and unpleasant surgical procedure and always involve a risk of complications. In addition, this is accompanied by a relatively long recovery period and the shape of for example a flat or short face above the lower jaw will usually remain largely unchanged.

The invention aims to remedy these disadvantages by proposing a bone anchor adapted to a patient which makes it possible to treat young patients, in particular younger than about 11 years old, and patients with a rather weak bone structure. In particular, the invention makes it possible to manufacture a bone anchor which can be used in very young patients and in patients having a weak or stunted bone structure in order to perform an orthopaedic or orthodontic treatment.

In addition, the invention aims to propose a bone anchor with an optimal shape, with an optimal orientation and position of screws, in order to achieve a firm anchoring, whereby the bone anchor can be subjected to relatively large forces without coming loose.

In order to manufacture a bone anchor and a corresponding drilling template according to the invention:
  a three-dimensional digital image of the bone is generated;
  on the basis of this three-dimensional image is selected a position and orientation for each of the aforesaid one or several screws as a function of the structure and density of the bone. Said position and orientation thus define a borehole with a borehole axis for said screws in relation to said bone;
  starting from said three-dimensional digital image and the selected position and orientation for said one or several screws, said anchor plate is designed with, for each of said screws, a recess having an axis which coincides with said borehole axis so as to make it possible to fix the anchor plate to said bone through this recess with said screws. The bone side of the anchor plate hereby connects to the surface of the bone, whereby said screws extend in the bone according to the selected position and orientation.

Further, said drilling template is designed with, for each of said screws, a cylindrical recess with a central axis for guiding a drill or cutter.

This method according to the invention is characterised in that the shape of the drilling template is designed such that it can be placed to fit against said free side of the anchor plate, whereas the aforesaid borehole axis coincides for each of the screws with the aforesaid central axis of the corresponding cylindrical recess. The diameter of said cylindrical recess is hereby made equal to or larger than the diameter of the head of the corresponding screw.

After the drilling template and the bone anchor have thus been designed, they will be produced, preferably by means of a rapid prototyping production method, such as for example an additive manufacturing technique.

According to a preferred embodiment of the method according to the invention, said drilling template is placed against the free side of the anchor plate of the bone anchor, such that the axis of the recesses of the anchor plate coincides with the aforesaid central axis of the corresponding cylindrical recesses in the drilling template, and the latter are then detachably connected to one another.

According to an interesting embodiment of the method according to the invention, said bone includes at least a portion of an upper and/or lower jaw against which said anchor plate must be attached. To said three-dimensional digital image of the bone is thus added a three-dimensional digital image of at least one tooth which is present in the jaw concerned, whereby during the design of said drilling template, a surface is provided on this drilling template which univocally connects to said at least one tooth.

Said three-dimensional digital image of the aforesaid at least one tooth is preferably obtained by optically scanning it or by scanning a physical model of the jaw with said at least one tooth. This three-dimensional image of said at least one tooth is added to said image of the bone by incorporating it in that image.

According to a major embodiment of the method according to the invention, an elongated connecting element with a mounting element for mounting orthodontic, orthopaedic or other tools is provided on said anchor plate, whereby this connecting element connects the mounting element to the anchor plate and must extend through gingiva or mucosa into the oral cavity.

In an advantageous manner, said drilling template is placed against the free side of the anchor plate of the bone anchor, such that the axis of the recesses of the anchor plate coincides with said central axis of the corresponding cylindrical recesses in the drilling template. Next, a depression is milled in the surface of the anchor plate for the head of each of said one or several screws by guiding a cutter through the corresponding cylindrical recess, whereby a depression is obtained whose dimensions correspond to those of the head of the corresponding screw.

In an interesting manner, said drilling template is placed against the free side of the anchor plate of the bone anchor, such that the axis of the recesses of the anchor plate coincides with said central axis of the corresponding cylindrical recesses in the drilling template, whereby said recesses are drilled in the anchor plate by means of a drill while the latter is being guided in the corresponding cylindrical recess of the drilling template.

The invention also concerns a set with a drilling template and at least one bone anchor and one or several screws for fastening the bone anchor to a bone. This bone anchor has an anchor plate with recesses for said screws provided with screw heads in order to fix the anchor plate to the surface of the bone. The anchor plate has a bone side which is to be connected to the surface of the bone and a free side opposite to said bone side. Further, the drilling template, for each of said screws, has a cylindrical recess with a central axis for guiding a drill or a cutter.

This set is characterised in that the shape of the drilling template makes it possible to place it in a fitting manner against said free side of the anchor plate, such that the central axis of each of the cylindrical recesses coincides with the axis of a corresponding recess in the anchor plate. The diameter of the cylindrical recesses is hereby equal to or larger than the diameter of the head of the corresponding screw.

Other particularities and advantages of the invention will become clear from the following description of some specific embodiments of the method and the set according to the invention. This description is given as an example only and does not limit the scope of the claimed protection in any way; the reference figures used hereafter refer to the accompanying figures.

In the different figures, the same reference figures refer to identical or analogous elements.

The invention generally concerns a bone anchor and an accompanying drilling template for fixing the bone anchor to the bone. The bone anchor and the drilling template are designed and manufactured as a function of the shape and structure of the bone on which the bone anchor is to be fixed. Thus, this can be used for any bone or bone part of a human or animal body.

Although the application of the invention is not limited to a specific bone part, it is particularly interesting to be applied to an upper and/or lower jaw. Thus, in the sequel of this description, the application to a jaw will be described as an example.

Figure 1:
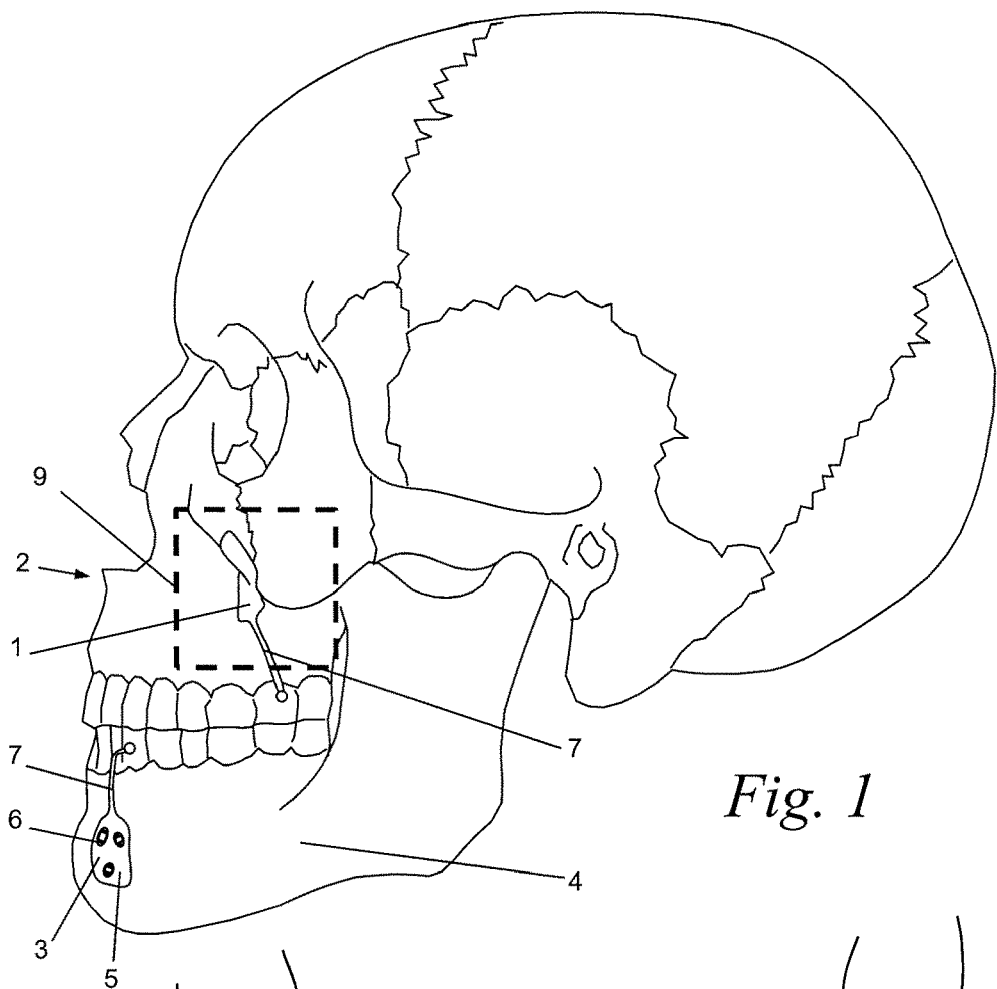
FIG. 1 is a schematic side view of a scull with a bone anchor on the upper jaw and on the lower jaw.
Figure 2:
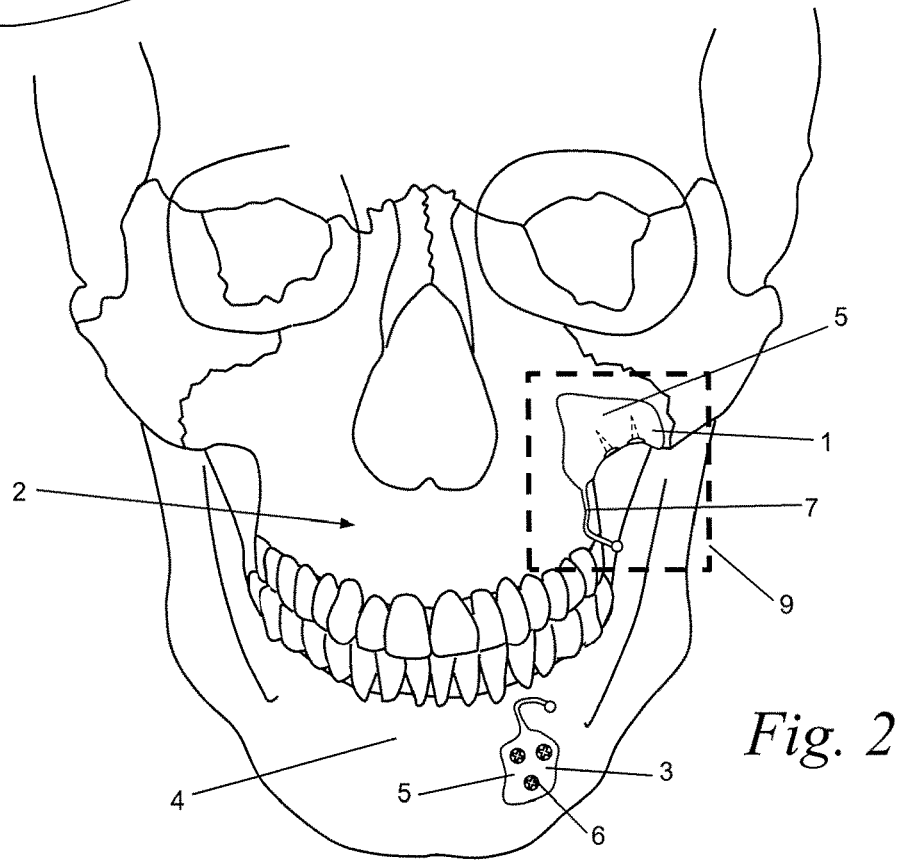
FIG. 2 is a schematic front view of the scull from FIG. 1.

FIGS. 1 and 2 schematically represent a scull wherein a first bone anchor 1 is fixed to the upper jaw 2 and a second bone anchor 3 is fixed to the lower jaw 4. These bone anchors 1 and 2 have an anchor plate 5 attached with screws 6 to the jaw concerned. This anchor plate 5 is adapted to the bone, in particular to its shape, whereby the bone side of the anchor plate 5 connects in a fitting manner to the surface of the bone.

The bone anchors 1 and 2 have an elongated connecting element 7 which connects the anchor plate 5 to a mounting element 8. The latter must be connected to orthodontic or orthopaedic tools, as has already been described for example in document WO 02/091941.

The connecting element 7 must extend into the oral cavity, such that the mounting element 8 is situated in the oral cavity. The connecting element 7 hereby protrudes through fixed gingiva or through the transition between fixed gingiva and loose mucosa. There where the connecting element 7 protrudes through this gingiva or mucosa, it preferably has a circular cross section.

In order to manufacture such a bone anchor 1 or 2 which is individually adapted to the bone of a patient, a three-dimensional digital image of the bone is generated. This is done, for example, by making a cone beam CT scan of the bone on which the bone anchor is to be placed.

When a bone anchor is to be placed on a jaw bone, also the present teeth are preferably recorded in the scan image.

Figure 3:
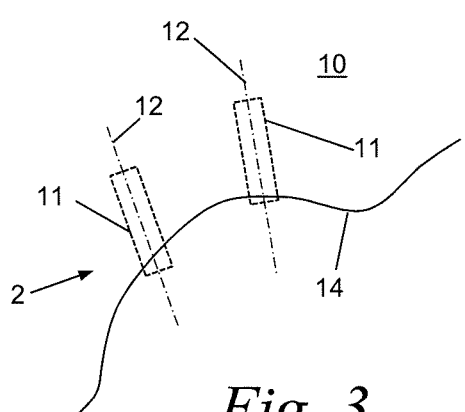
FIG. 3 is a schematic view of a dimensional image of a part of a bone on which a bone anchor is to be placed.

FIG. 3 schematically represents a view of the bone 10 of the upper jaw 2 from FIGS. 1 and 2. More specifically, this figure schematically represents the three-dimensional image of the part of the upper jaw 2 which is indicated in FIGS. 1 and 2 by a rectangle 9.

In this three-dimensional image, the structure of the bone 10 is visible (not represented in the figure). Thus, the cortical bone thickness and the density of the bone 10 can be derived from this image.

On the basis of this three-dimensional image, a position and orientation are selected for each of the screws as a function of the structure and density of the bone. More specifically, a location with optimal bone quality is selected, meaning a location with a cortical bone thickness that is as high as possible and a bone density that is as high as possible. The position and orientation, as well as the diameter and length of the screws to be used are thus selected as a function of the location having the best possible bone quality. In this manner is defined a borehole 11 for every screw 6 having a borehole axis 12 in relation to said bone 10.

Figure 4:
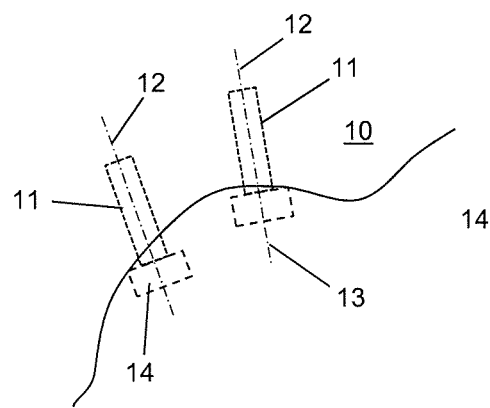
FIG. 4 represents the view from FIG. 3 in which a selected position and orientation for screws is schematically represented.

Next, a disc-shaped volume 13 with a circular section is selected which should contain the heads of the screws 6 concerned. This volume 13 is placed against the surface 14 of the bone 10 when designing the bone anchor, as represented in FIG. 4. It is made sure hereby that the axis of this volume 13 coincides with the borehole axis 12.

Figure 5:
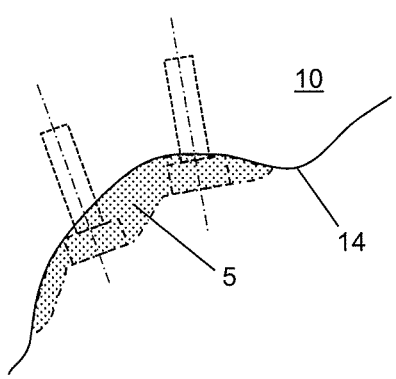
FIG. 5 represents the view from FIG. 4 in which a design for an anchor plate is additionally represented.

On the basis of this three-dimensional digital image and the selected position and orientation for said screws 6, the anchor plate 5 is then designed. The position of said volumes 13 thus defines, for each of the screws 6, a recess with an axis which coincides with the borehole axis 12. These recesses make it possible to fix the anchor plate 5 to the bone 10 by means of the screws 6. The anchor plate 5 is designed such that it connects the different volumes 13 to one another. In this design it is ensured that the bone side 15 of the anchor plate 5 connects to the surface 14 of the bone 10, as is schematically represented in FIG. 5.

Figure 6:
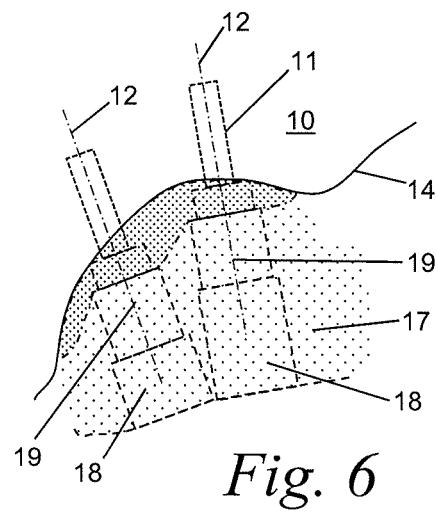
FIG. 6 represents the view from FIG. 5 in which a design for a drilling template is additionally represented.

Next, the drilling template 17 is designed, as is represented in FIG. 6. For each of the screws 6, or for each borehole 11, a cylindrical recess 18 having a central axis 19 is hereby provided in the drilling template 17. The borehole axis 12 for each of the screws 6 hereby coincides with the central axis 19 of the corresponding cylindrical recess 18. The diameter of these cylindrical recesses is equal to or larger than the diameter of the head of the corresponding screw 6.

The cylindrical recesses 18 are thus designed such that, on the one hand, they make it possible to guide a drill or a cutter and, on the other hand, said screws 6 can be screwed in the bone through these recesses 18.

Further, in the design of the drilling template 17 it is made sure that the latter can connect to the free side 16 of the anchor plate 5 in a fitting manner, as is represented in FIG. 6, whereby the borehole axis 12 for each of the screws 6 coincides with the central axis 19 of the corresponding cylindrical recess 18.

It should be further mentioned in this context that the drilling template 17 does not have to connect in a fitting manner to the free surface of the anchor plate 5 over a continuous surface, as is represented in FIGS. 6 to 10. Thus, it is for example possible for the drilling template 17 to connect to the free surface of the anchor plate 5 only via one or several contact zones. Such contact zones may connect for example to the recesses 18 or the open end of the latter.

After the drilling template 17 and the bone anchor with the anchor plate 5 have thus been designed, whereby the drilling template can be connected to the free side of the anchor plate, they are manufactured. This is preferably done by means of a rapid prototyping technique such as an additive manufacturing method. The bone anchor is for example made of titanium produced by means of selective laser melting production (SLM). The drilling template 17 can be manufactured in the same way, but it can also be made of plastic.

Figure 7:
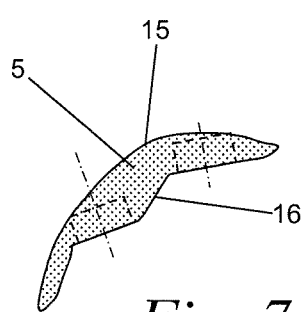
FIG. 7 is a schematic view of an anchor plate manufactured according to the method of the invention.
Figure 8:
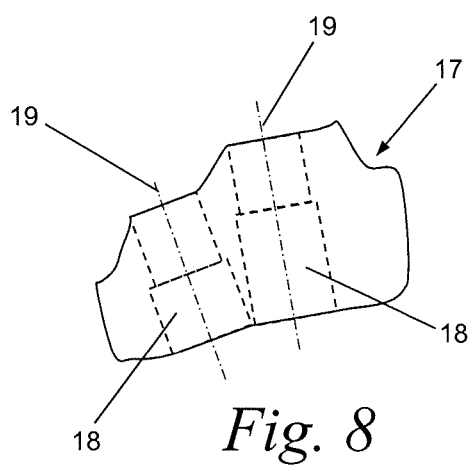
FIG. 8 is a schematic view of a drilling template manufactured according to the method of the invention.

FIG. 7 schematically represents a side view of an anchor plate 5 of a bone anchor, whereas FIG. 8 represents a schematic side view of the accompanying drilling template 17.

In order to be able to place the drilling template 17 in a univocal and stable manner in the oral cavity, it may additionally have a surface which can be provided over the teeth of the corresponding jaw in a fitting manner.

Since the surfaces of teeth are often not sharply displayed in a cone beam CT scan, a three-dimensional digital image of the teeth is advantageously added to the already generated three-dimensional digital image of the bone.

To this end, for example a three-dimensional digital image is generated by laser scanning the teeth or a physical model of the teeth, such as a gypsum model.

This three-dimensional digital image of the teeth is then merged with the three-dimensional digital image of the bone by applying, for example, a 'best fit' algorithm.

Naturally, instead of teeth, other reference elements in the oral cavity may be used so as to be able to place the drilling template 17 in a uniform and stable manner in the oral cavity. The drilling template is then provided with a corresponding surface which can be placed against one or several of these reference elements.

Figure 9:
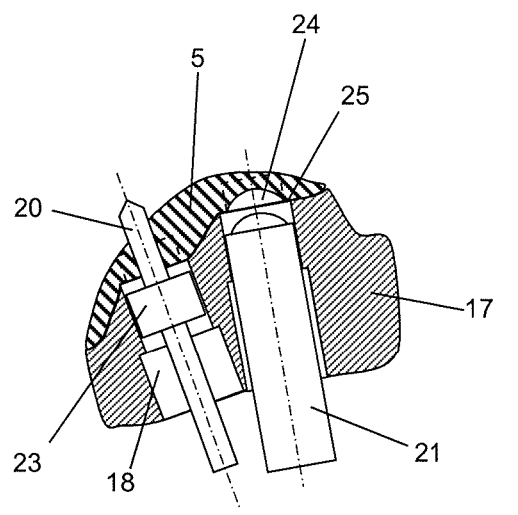
FIG. 9 is a schematic cross section of a drilling template and an anchor plate placed against one another in a fitting manner.

FIG. 9 schematically represents a drill 20 and a cutter 21 while the anchor plate 5 is being manufactured. Once the anchor plate 5 from FIG. 7 and the drilling template 17 from FIG. 8 have been obtained, they are placed against one another as represented in FIG. 9.

The drilling template 17 is hereby placed against the free side 16 of the anchor plate 5 of the bone anchor, such that the axis of the recesses to be provided in the anchor plate 5 coincides with said central axis 19 of the corresponding cylindrical recesses 18 in the drilling template 17. This implies that the axis of the volume 13 coincides with the central axis 19 of the cylindrical recesses 18. Next, the recesses 22 for the screws 6 are provided in the anchor plate 5 by guiding a drill 20 through the corresponding cylindrical recesses 18. To this end, the drill 20 has a cylindrical coaxial guide 23 which is guided in the cylindrical recesses 18 in a fitting and coaxial manner.

The heads of the screws 6 are preferably countersunk in the free side 16 of the anchor plate 5. Thus, when the drilling template 17 is placed against the free side of the anchor plate 5, a depression 24 is milled in the surface of the anchor plate 5 by guiding a cutter 21 through the corresponding cylindrical recess 18. Thus is obtained a depression 24 whose dimensions correspond to those of the head of the corresponding screw 6, as is schematically represented in FIG. 9.

In order to make sure that the cutter 21 shapes a depression 24 with a proper depth, the diameter of the cylindrical recesses 18 must be slightly larger than that of the volumes 13 or than the diameter of the screw heads, such that the surface of the free side 16 of the anchor plate 5 which connects to this volume 13 forms a stop 25 for the cutter 21.

Naturally, the recesses 22 and the depressions 24 must not necessarily be provided by drilling or by milling as described above, but they can also be provided by manufacturing the bone anchor with the anchor plate 5 by means of a rapid prototyping technique such as for example an additive manufacturing technique, more specifically SLM.

Figure 10:
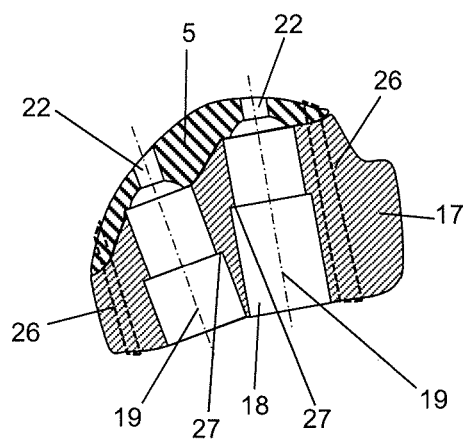
FIG. 10 is a schematic cross section of a drilling template with an accompanying anchor plate which are detachably connected to one another.

In order to fix the bone anchor to the bone 10 of the jaw, the drilling template 17 is placed against the free side 16 of the anchor plate 5 of the bone anchor, as represented in FIG. 10. These are placed against one another in such a way that the axis of the recesses 22 of the anchor plate 5 coincides with the central axis 19 of the corresponding cylindrical recesses 18 in the drilling template 17. Next, the bone anchor and the drilling template 17 are connected to each other in a detachable manner.

To this end, the drilling template 17 protrudes for example laterally from the anchor plate 5 of the bone anchor. Through the drilling template 17 and laterally with respect to the anchor plate 5 are provided ducts through which a thin loop-shaped wire 26 is inserted which runs over the bone side of the anchor plate. Thus, this wire 26 connects the anchor plate 5 to the bone anchor 17. Such a wire may for example consist of a steel wire having a diameter of 0.010".

After the drilling template 17 has thus been connected to the bone anchor in a detachable manner, the drilling template 17 is positioned in the oral cavity, whereby the anchor plate 5 rests against the surface 14 of the bone 10. Naturally, the bone 10 must first be exposed by means of a surgical procedure by temporarily displacing tissue.

Next, the bore holes 11 are provided by guiding a drill through the different cylindrical recesses 18 of the drilling template 17. This drill has for example a cylindrical collar which is guided through the cylindrical recesses 18 while drilling until a stop 27 for this collar is reached in the recess 18.

In the embodiment of the invention represented in the figures, this stop 27 consists of an annular surface with a central axis which coincides with the central axis 19 of the cylindrical recesses 18.

After the boreholes have thus been drilled according to the predetermined depth, orientation and diameter, a screw is screwed in the borehole through each of the cylindrical recesses 18 of the drilling template 17. The heads of the screws 6 in the depression 24 hereby rest in the surface of the anchor plate 5, such that the latter is fixed to the bone.

Next, the wire 26 is pulled out of the drilling template, such that it can be removed from the anchor plate 5 and such that the drilling template can be removed as well from the anchor plate 5.

Finally, the screws 6 can possibly be tightened somewhat further once the drilling template has been removed, and the anchor plate is coated with the previously displaced tissue.

The invention claimed is:

1. A method for manufacturing at least one bone anchor and a corresponding drilling template, wherein the bone anchor has an anchor plate which is to be fixed with one or several screws provided with screw heads against the surface of a bone, such that the anchor plate has a bone side which is to be connected to the surface of the bone and a free side opposite to said bone side, the method comprising:
   a) generating a three-dimensional digital image of the bone;
   b) selecting, on the basis of this three-dimensional image, a position and orientation for each of said one or several screws for fixing the anchor plate to the surface of the bone as a function of the structure and density of the bone, wherein a borehole with a borehole axis is thus defined for said screws in relation to said bone;
   c) designing, starting from said three-dimensional digital image and the selected position and orientation for said one or several screws, said anchor plate with, for each of said screws, a recess in the anchor plate with an axis which coincides with said borehole axis in order to make it possible for the anchor plate to be fixed to said bone through this recess in the anchor plate by said screws, such that its bone side connects to the surface of the bone, wherein said screws extend in the bone according to the selected position and orientation,
   d) designing the shape of the drilling template so as to be placed against said free side of the anchor plate, and designing said drilling template with, for each of said screws, a cylindrical recess in the drilling template having a central axis for guiding a drill or a cutter,
   wherein said borehole axis for each of the screws for fixing the anchor plate to the surface of the bone coincides with said central axis of the corresponding cylindrical recess of the drilling template and the central axis of the cylindrical recess of the drilling template coincides with the axis of the recess in the anchor plate,
   wherein the diameter of said cylindrical recess of the drilling template is equal to or larger than the diameter of the head of the corresponding screw and larger than the diameter of the corresponding recess of said anchor plate, and
   e) manufacturing the drilling template and the bone anchor according to the designs in steps c)-d).

2. The method according to claim 1, wherein said drilling template is placed against the free side of the anchor plate of the bone anchor and, subsequently, the bone anchor and the drilling template are connected to one another in a detachable manner, such that the axis of the recesses of the anchor plate coincides with said central axis of the corresponding cylindrical recesses in the drilling template.

3. The method according to claim 1, further comprising providing said cylindrical recesses in the drilling template with a stop for a drill so as to make it possible to provide boreholes in said bone which have a predetermined depth.

4. The method according to claim 1, wherein said bone includes at least a part of an upper or lower jaw against which said anchor plate is to be fixed and further comprising adding, to said three-dimensional digital image of the bone, a three-dimensional digital image of at least one tooth which is present in said jaw, wherein said step of designing said drilling template comprising providing a surface to this drilling template which univocally connects to said at least one tooth.

5. The method according to claim 4, further comprising taking a cone beam CT scan of said jaw so as to generate said three-dimensional digital image of the bone.

6. The method according to claim 4, further comprising obtaining said three-dimensional digital image of said at least one tooth by optically scanning it or by scanning a physical model of the jaw with said at least one tooth, wherein said three-dimensional image of said at least one tooth is added to said image of the bone by incorporating said three-dimensional image in said image of the bone.

7. The method according to claim 1, further comprising providing an elongated connecting element with a mounting element for mounting orthodontic or orthopaedic means on said anchor plate, wherein said connecting element connects the mounting element to the anchor plate and extends through gingiva or mucosa into the oral cavity.

8. The method according to claim 1, further comprising placing said drilling template against the free side of the anchor plate of the bone anchor, such that the axis of the recesses of the anchor plate coincides with said central axis of the corresponding cylindrical recesses in the drilling template, and subsequently drilling said recesses in the anchor plate by a drill while guiding the drill in the corresponding cylindrical recess of the drilling template.

9. The method according to claim 1, further comprising placing said drilling template against the free side of the anchor plate of the bone anchor, such that the axis of the recesses of the anchor plate coincides with said central axis of the corresponding cylindrical recesses in the drilling template, and subsequently, for the head of each of said one or several screws, milling a depression in the surface of the anchor plate by guiding a cutter through the corresponding cylindrical recess, wherein a depression is obtained whose dimensions correspond to those of the head of the corresponding screw.

* * * * *